(12) United States Patent
Ben-Menahem et al.

(10) Patent No.: US 7,571,056 B2
(45) Date of Patent: Aug. 4, 2009

(54) ANALYZING INFORMATION GATHERED USING MULTIPLE ANALYTICAL TECHNIQUES

(75) Inventors: Shahar Ben-Menahem, Pasadena, CA (US); James Kelly Breaux, Pasadena, CA (US); Sandeep Gulati, La Canada, CA (US); Thomas George, La Canada, CA (US); Clare Livingston Bromley, III, Del Mar, CA (US)

(73) Assignee: ViaLogy Corp., Altadena, CA (US)

( * ) Notice: Subject to any disclaimer, the term of this patent is extended or adjusted under 35 U.S.C. 154(b) by 43 days.

(21) Appl. No.: 11/753,444

(22) Filed: May 24, 2007

(65) Prior Publication Data

US 2008/0015793 A1 Jan. 17, 2008

Related U.S. Application Data

(60) Provisional application No. 60/808,351, filed on May 25, 2006.

(51) Int. Cl.
*G01N 31/00* (2006.01)
*H04B 15/00* (2006.01)

(52) U.S. Cl. ........................................ 702/30; 702/189

(58) Field of Classification Search .................. 702/23, 702/30, 67, 179, 181, 189, 66; 703/9, 11, 703/12
See application file for complete search history.

(56) References Cited

U.S. PATENT DOCUMENTS 4,353,242 A * 10/1982 Harris et al. ............... 73/23.36

2007/0016389 A1 * 1/2007 Ozgen .......................... 703/10

FOREIGN PATENT DOCUMENTS

WO 2007/140270 * 12/2007

OTHER PUBLICATIONS van Dyk, D. A. et al. "Analysis of Energy Spectra with Low Photon Counts via Bayesian Posterior Simulation," The Astrophysical Journal, vol. 548, p. 224-243, Feb. 10, 2001.
H.H. Willard, L L. Merritt, J.A. Dean, and F.A. Settle. 1998. "Mass Spectrometry." 7th Edition, *Instrumental Methods of Analysis*. Wadsworth Publishing Company. pp. 465-485.
J.R. de Laeter. 2001. "Inductively Coupled Plasma Mass Spectrometry." John Wiley & Sons, Inc. *Applications of Inorganic Mass Spectrometry*. pp. 68-70.
"Introduction to Mass Spectrometry (MS)" [online], [retrieved on Jun. 8, 2007]. Retrieved form the Internet: <URL: http//elchem.kaist.ac.kr/vt/chem.-ed/ms/ms-intro.htm>.
Jonscher et al. "The Whys and Wherefores of Quadrupole Ion Trap Mass Spectrometry", ABRF News, Sep. 1996, [online], [retrieved on Jun. 8, 2007]. Retrieved form the Internet: <URL: www.abrf.org/ABRFNews/1996/September1996/sep96iontrap.html>.
"Introduction to Mass Spectrometry" [online], [retrieved on Jun. 8, 2007]. Retrieved form the Internet: <www.chem.arizona.edu/massspec/intro_html/intro.html>.

* cited by examiner

*Primary Examiner*—Michael P Nghiem
(74) *Attorney, Agent, or Firm*—Fish & Richardson P.C.

(57) ABSTRACT

Systems and techniques for analyzing information gathered by multiple analytical techniques. In one aspect, a method includes receiving analytical information, gathered by multiple analytical techniques, regarding a sample, receiving expectations regarding a sample parameter, and estimating a value of the sample parameter based on the analytical information and the expectations regarding the sample parameter.

17 Claims, 13 Drawing Sheets

ANALYZING INFORMATION GATHERED USING MULTIPLE ANALYTICAL TECHNIQUES

CROSS-REFERENCE TO RELATED APPLICATIONS

Under 35 U.S.C. § 119(e), this application claims the priority of U.S. Provisional Application Ser. No. 60/808,351, filed May 25, 2006, entitled "Increased Sensitivity in GC/MS using a novel "Swept Window" Maximum A Posteriori Probability (MAP) Technique", the contents of which are incorporated herein by reference.

BACKGROUND

This disclosure relates to analyzing information gathered using multiple analytical techniques.

Analysis of chemical samples can yield a wide variety of information regarding the samples. The information can include, e.g., the identity of constituent components, the quantities of constituent components, time information such as the rate of change of the composition of the chemical sample, position information such as the physical disposition of constituent components within the sample, and detailed chemical information, such as the stability of the constituent components and the nature of interactions between constituent components.

Although chemical samples can yield such a wide variety of information, the actual information gathered by any one analytical technique is often quite limited. For example, a pH meter gathers information regarding the concentration of hydrogen ions in a chemical sample (i.e., how "acidic" a sample is). As another example, mass spectrometry gathers information regarding the mass-to-charge ratio of charged species generated from a sample. As yet another example, chromatography gathers information regarding interactions between the constituent components of a sample and a stationary phase.

The information gathered by multiple analytical techniques can be combined to improve the characterization of a chemical sample. FIG. 1 is an example of a combination of information gathered by multiple analytical techniques, namely, a graph 100. Graph 100 includes an axis 105, an axis 110, and a number of peaks 115, 120, 125, 130. Position along axis 105 embodies the mass-to-charge ratio of charged species generated from the sample, as determined by mass spectrometry. Position along axis 110 embodies the strength of the interactions between the constituent components of the sample and a stationary phase, as determined by gas chromatography. The strength of the interactions between the constituent components is denoted as a "scan number" that indicates the number of a mass spectrometry scan in a series of such scans that were made on the effluent of a chromatograph. Peaks 115, 120, 125, 130 each represent different constituent components of the sample.

The combination of mass-to-charge ratio information and interaction strength information in graph 100 can improve the characterization of the sample. For example, peaks 115, 120 overlap at position P1 along axis 105. This overlap indicates that the charged species generated from the constituent components represented by peaks 115, 120 have the same mass-to-charge ratio. If only mass-to-charge ratio information were available, peaks 115, 120 (and the constituent components that they represent) would be indistinguishable. However, the interaction strength information provided by gas chromatography allows peaks 115, 120 and the constituent components that they represent to be distinguished.

As another example, peaks 125, 130 overlap at position P2 along axis 110. This overlap indicates that the constituent components represented by peaks 125, 130 have the same strength of the interaction with a stationary phase. If only strength of the interaction information were available, peaks 125, 130 (and the constituent components that they represent) would be indistinguishable. However, the mass-to-charge information provided by mass spectrometry allows peaks 125, 130 and the constituent components that they represent to be distinguished.

SUMMARY

The present inventors have recognized that information gathered by multiple analytical techniques can be analyzed using statistical methods that are based on subjective expectations regarding the meaning of that information. For example, Bayesian statistics, such as maximum a posteriori (MAP) estimation, can be used to improve signal-to-noise ratios in combinations of information gathered by chromatography and mass spectroscopy.

In one aspect, a method for analyzing information gathered by multiple analytical techniques includes receiving analytical information, gathered by multiple analytical techniques, regarding a sample, receiving expectations regarding a sample parameter, and estimating a value of the sample parameter based on the analytical information and the expectations regarding the sample parameter.

This and other aspects can include one or more of the following features. The value of the sample parameter can be estimated by estimating the value using Bayesian statistics. The value of the sample parameter can be estimated by generating a maximum a posteriori (MAP) estimation of the value of the sample parameter.

The analytical information can include a surface representing analytical information gathered by mass spectrometry and chromatography. The value of the sample parameter can be estimated by sweeping a window objective function across an analytical information space that represents the analytical information gathered by multiple analytical techniques. The window objective function can be a two-dimensional window objective function that is swept across a two-dimensional analytical information surface. The window objective function can include a function that includes a parameter representing simulated mass-selected information, a function that includes a parameter representing non-mass-selected information, and/or a function that includes a parameter representing real chromatographic information. A collection of derivative attributes at different positions can be determined. The collection of derivative attributes can be assembled into a new derivative space and the collection of derivative attributes can be made available.

In another aspect, an article includes one or more machine-readable media storing instructions operable to cause one or more machines to perform operations. The operations can include sweeping a window objective function across an analytical information space that represents information gathered by multiple analytical techniques, inferring a derivative attribute for each of a collection of positions along the sweep using the window objective function and the information gathered by the multiple analytical techniques, and combining the derivative attributes for the collection of positions into a derivative space.

This and other aspects can include one or more of the following features. The derivative attributes can be assigned to foci of the window objective function at each of the positions in the collection of positions. The analytical information space can be a two-dimensional surface. The window objective function can be a two-dimensional window objective function. The derivative attributes can be combined by combining the derivative attributes into a derivative surface. The analytical information space can represent a mass-to-charge ratio of charged species generated from a sample and interactions between constituent components of the sample and a stationary phase.

The window objective function can include a function that includes a parameter representing simulated mass-selected information and a parameter representing non-mass-selected information.

The derivative attributes can be combined by combining derivative attributes representing mass-selected species into the derivative space. The derivative attributes can be inferred generating a maximum a posteriori (MAP) estimation of the value of the derivative attribute. The derivative space can be made available.

The details of one or more implementations are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Bayesian statistics states that estimates of the probability that a proposition is true are related to the subjective expectations regarding the proposition. For example, estimates of the probability that it will rain tomorrow can be related to subjective expectations regarding the meaning of current wind direction, geographic location, current humidity, etc. Such subjective expectations can be expressed as a prior probability distribution that sets forth the expectations regarding a variable in the absence of current set of evidence. For example, a prior probability distribution can sets forth the expectations that it will rain tomorrow based on expectations regarding the level of humidity in the absence of information regarding the current level of humidity. In some cases, a human expert can make a rational assessment of the probability of an outcome based on established knowledge and before a set of present evidence is included.

The posterior probability distribution is the conditional probability that is assigned to a proposition when the set of present evidence is taken into account. For example, a posterior probability distribution can be assigned to a proposition that it will rain tomorrow when the current level of humidity is taken into account. According to Bayes' theorem, the prior probability distribution can be multiplied by a likelihood function and divided by a normalizing constant to arrive at the posterior probability distribution.

MAP estimation uses the mode of a posterior probability distribution to generate a point estimate of a parameter. The mode of a distribution is the most frequently occurring value in the distribution. A point estimate is a single estimated value of a parameter of a population.

Figure 2:
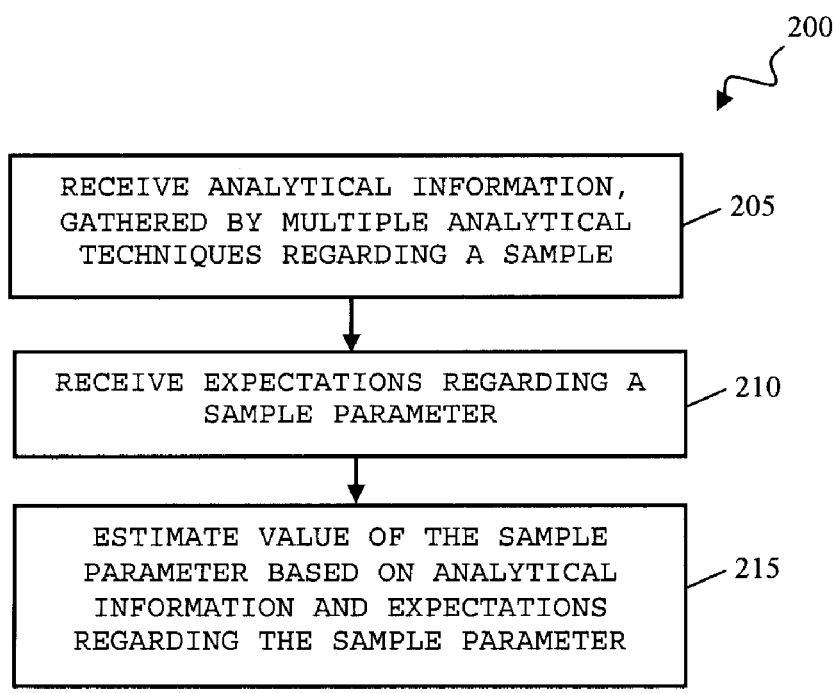
FIG. 2 is a flowchart of a process in which information gathered by multiple analytical techniques is analyzed using statistical methods that are based on subjective expectations regarding the meaning of that information.

FIG. 2 is a flowchart of a process 200 in which information gathered by multiple analytical techniques is analyzed using statistical methods that are based on subjective expectations regarding the meaning of that information. Process 200 can be performed by a system of one or more data processing devices that perform data processing activities in accordance with the logic of a set of machine-readable instructions. For example, process 200 can be performed by a computer that is executing software.

The system performing process 200 can receive a collection of analytical information that has been gathered by multiple analytical techniques at 205. The received analytical information can regard a single sample and can include raw and/or processed data. For example, the received analytical information can be mass-to-charge ratio information gathered using mass spectrometry and interaction strength information gathered using chromatographic techniques, such as gas chromatography or liquid chromatography.

The system performing process 200 can also receive information describing the expectations regarding a sample parameter at 210. The expectations can relate to the relationship between analytical information of the same category as received at 205 (e.g., mass-to-charge ratio information, interaction strength information, etc.) and the sample parameter. The expectations can be expressed as a prior probability distribution that sets forth those expectations independently of the analytical information actually received at 205.

For example, in the context of mass spectrometry and chromatography, expectations regarding peaks that correspond to mass-selected species generated from a sample can be represented as a scan number dependent function. With the variable "s" representing the relative scan number and s=0 corresponding to the nominal scan number for the extracted ion chromatogram peak (e.g., 238 for octafluoronapthalene in a standard scan), expectations regarding a mass-selected species can be represented as:

$$\lambda(s) = \lambda_m \rho(s) \qquad \text{Equation 1}$$

where $\lambda(s)$ corresponds to the integrated abundance of the peak at a particular scan number "s" over the selected m/z values and $\lambda_m$ is the maximum integrated abundance. The term p(s) is a standard extracted ion chromatogram shape, with $\rho_{max}=1$. For a Guassian peak, Equation 1 can be expressed as:

$$\lambda(s) = \lambda_m \exp[-(s-b)^2/2c] \qquad \text{Equation 2}$$

where "b" is the actual scan number for $\lambda_m$ (in case it is shifted) and "c" is the square of the variance of the extracted ion chromatogram peak.

As another example, in the context of mass spectrometry and chromatography, expectations regarding peaks that correspond to non-mass-selected species such as excited helium can be represented as a maximum likelihood parameter μ. The maximum likelihood parameter μ can model the "arrival times" (i.e., the m/z values) at which these peaks occur as a Guassian probability distribution. The maximum likelihood parameter μ can thus reflect the likely time intervals between non-mass-selected events.

The system performing process 200 can also estimate a value of the sample parameter based on the received analytical information and expectations at 215. The value of the sample parameter can be estimated using Bayesian statistical techniques, such as MAP estimation.

Figure 3:
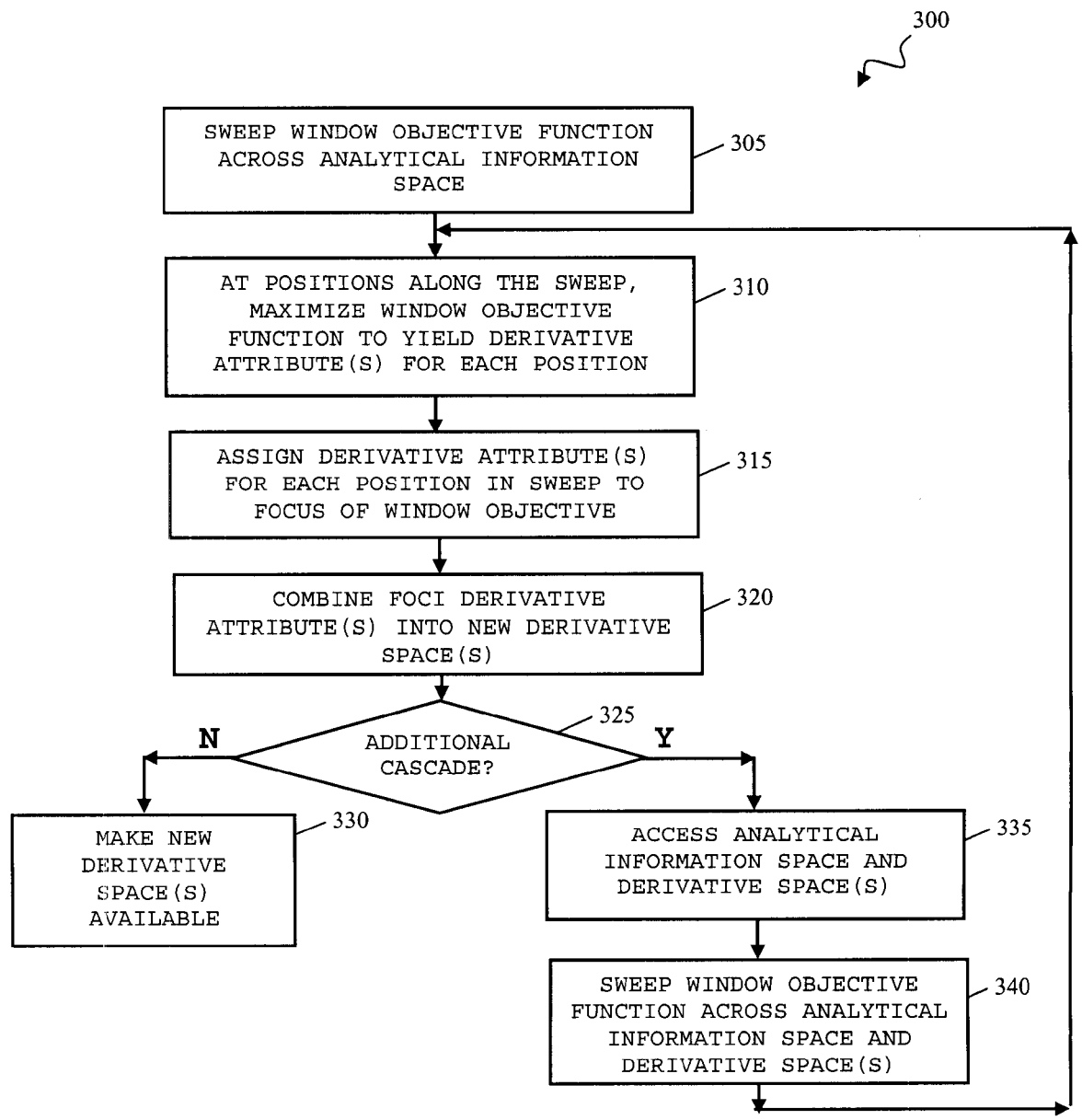
FIG. 3 is a flowchart of a process for estimating a value of a sample parameter based on analytical information and expectations regarding the relationship between analytical information of the same category and that sample parameter.

FIG. 3 is a flowchart of a process 300 for estimating a value of a sample parameter based on analytical information and expectations regarding the relationship between analytical information of the same category and that sample parameter. The analytical information can have been gathered by multiple analytical techniques.

Process 300 can be performed by a system of one or more data processing devices that perform data processing activities in accordance with the logic of a set of machine-readable instructions. Process 300 can be performed as a stand-alone process or in conjunction with other activities. For example, process 300 can be performed at 215 in process 200 (FIG. 2).

Figure 1:
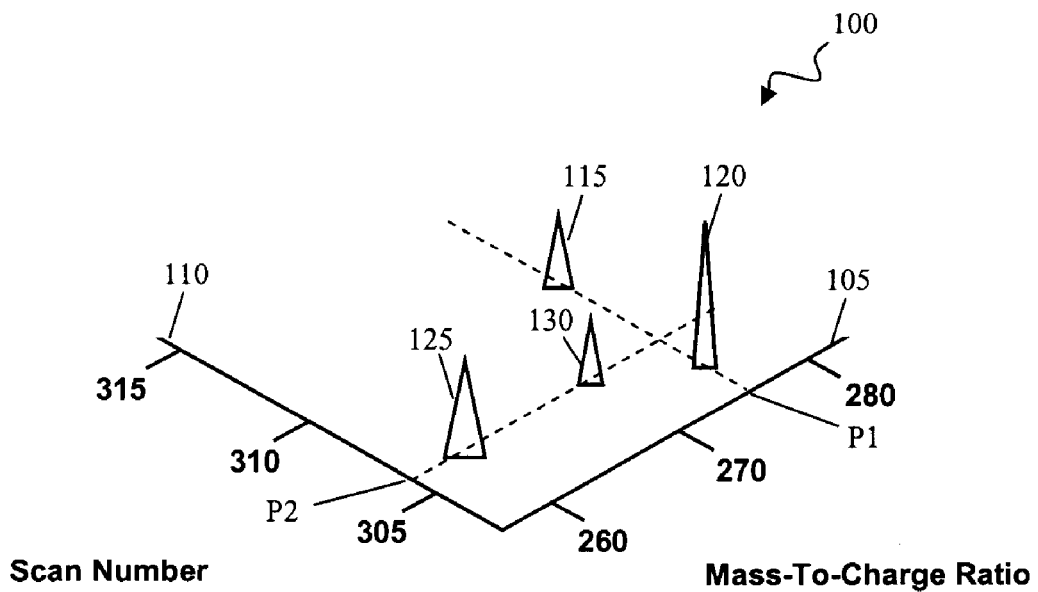
FIG. 1 is a graph that combines information gathered by multiple analytical techniques.

The system performing process 300 can sweep a window objective function across analytical information space at 305. Analytical information space is representation of the information gathered by multiple analytical techniques. For example, in FIG. 1, the analytical information space is the surface of graph 100 between axes 105, 110. The analytical information space in FIG. 1 is a two-dimensional surface that represents information from gathered by two analytical techniques (i.e., mass spectrometry and chromatography). However, information gathered using additional analytical techniques can be represented in additional dimensions of an analytical information space.

A window objective function represents expectation values of the sum of squares of the errors between the information represented in the analytical information space and a subjective match to that analytical information space. For example, Monte Carlo simulations can be used to make an assessment of the probability that analytical information space has a certain contour based on established knowledge regarding such contours, independently of the information actually represented in the analytical information space.

Figure 4:
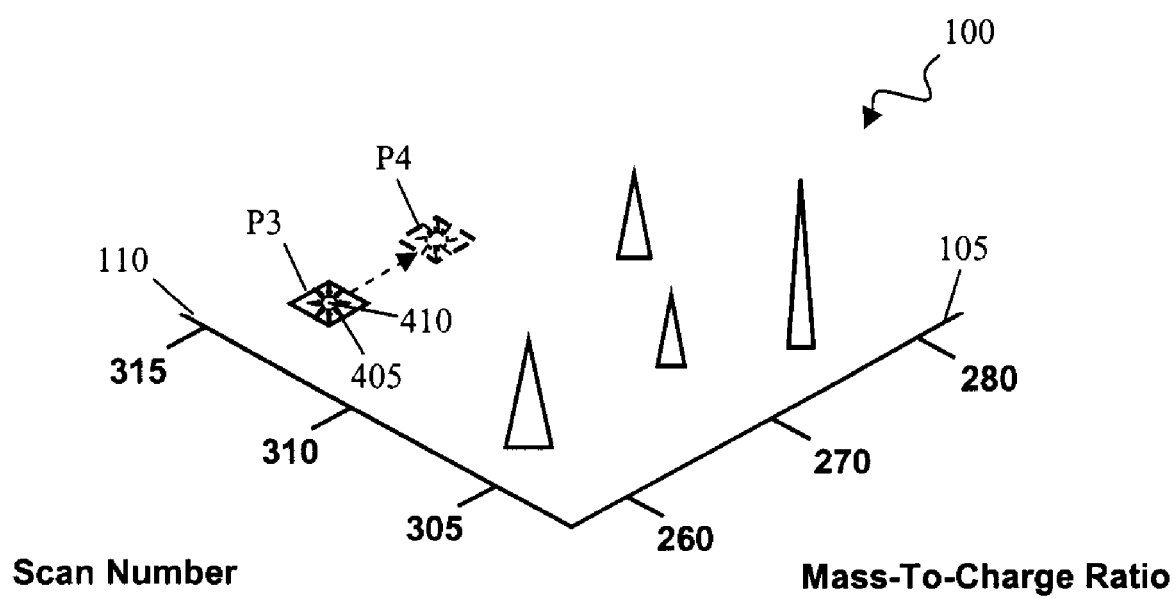
FIG. 4 is a schematic representation of sweeping a window objective function across the analytical information space of graph.

FIG. 4 is a schematic representation of sweeping a window objective function 405 across the analytical information space of graph 100. In particular, window objective function 405 is moved from a first position P3 to a second position P4. Window objective function 405 includes a focus 410. In some implementations, focus 405 can be positioned near the center of window objective function 405.

Returning to FIG. 3, the system performing process 300 can maximize the window objective function to infer one or more derivative attributes at different positions along the sweep at 310. Since the window objective function is an expectation value that quantifies the difference (i.e., errors) between the analytical information space and a subjective match to that analytical information space, maximizing the window objective function has the effect of minimizing the errors and estimating a value of the sample parameter at each position. Such estimates of a value are defined as derivative attributes.

In some implementations, multiple derivative attributes can be inferred for each position. The different derivative attributes estimate the value of different parameters of the sample. For example, as discussed further below, in the context of mass spectrometry and chromatography, derivative attributes that estimate the value of responses to mass-selected species and responses to non-mass-selected species can be inferred for each position.

The system performing process 300 can assign the derivative attribute(s) for each position to a focus of the window objective function at that position at 315. Once the derivative attribute(s) have been associated with foci, the foci derivative attribute(s) can be combined to create one or more new derivative spaces at 320. In the context of a two-dimensional surface that represents information gathered by two analytical techniques, the position of the foci can correspond to the position of pixels in a new, two-dimensional derivative surface.

The system performing process 300 can also determine if an additional cascade is to be performed at 325. Such a determination can be made based on input from a human user or automatically, i.e., in the absence of input from a human user. For example, the system can determine a signal-to-noise ratio of a new derivative space and compare it with a predefined metric to determine if an additional cascade is to be performed.

If the system performing process 300 determines that an additional cascade is not to be performed, the system can make the new derivative space(s) available at 330. For example, the new derivative space(s) can be provided to an allied data processing device for further data processing activities. As another example, the new derivative space(s) can be output for display to a human user.

If the system performing process 300 determines that an additional cascade is to be performed, the system can access both the analytical information space and one or more of the new derivative space(s) at 335. The system performing process 300 need not access every new derivative space that was created at 320. For example, in the context of mass spectrometry and chromatography, a new derivative space that represents estimates of the values of responses to mass-selected species can be accessed whereas a new derivative space that represents estimates of the values of responses to non-mass-selected species can be excluded from access.

The system performing process 300 can sweep a window objective function across both the analytical information space and one or more of the new derivative space(s) at 340.

In some implementations, the information from the analytical information space and one or more of the new derivative space(s) can be used to populate arrays that encode sample parameters. For example, in the context of mass spectrometry and chromatography, the arrays can encode how many ions/molecules arrived in a scan, the arrival times of these ions/molecules, and how many ions/molecules arrived per each given m/z in the scan line within or near the window objective function boundary.

The window objective function swept at 340 can differ from the window objective function swept at 305. For example, the dimensions of the window, the location of the focus within the window, and the expectations represented by the window objective function can be changed.

The system performing process 300 can maximize the window objective function at different positions along the sweep at 310, assign the derivative attribute(s) for each position to a focus at 315, and combine the foci derivative attribute(s) to create one or more new derivative spaces at 320. If the system performing process 300 determines that an additional cascade is not to be performed at 325, the system can make the new derivative space(s) available at 330. The new derivative space(s) can be made available in a number of ways. For example, in the context of mass spectrometry and chromatography, derivative attributes that estimate the value of responses to mass-selected species at corresponding positions in different derivative spaces can be added together before they are made available.

In the context of mass spectrometry and chromatography, the window objective function $\Psi$ given in Equation 3 can be used, where $\Psi_s$ depends on the parameters to be optimized and can be evaluated at each m/z point, at steps of, e.g., 0.1 amu.

$$-\psi = -\sum_{s=-3}^{3} \psi_s \qquad \text{Equation 3}$$

In some implementations, the parameters to be optimized can correspond to simulated mass-selected peaks, simulated non-mass-selected peaks, and real chromatographic data peaks.

$$-\psi = -\sum_{s=-3}^{3} E\left[\int_{-2.3}^{2.7} dt \left\{ \begin{array}{c} g\sum_{i=1}^{n}\xi(t-\tau_i) + g\sum_{j=1}^{m}\xi(t-t_j) - \\ g_0 \sum_{k=1}^{n_0(s)} \xi(t-t_k^{(0)}) \end{array} \right\}^2 \right] \qquad \text{Equation 4}$$

Equation 4 is an example expansion of the window objective function $\Psi$, where:

$$g\sum_{i=1}^{n}\xi(t-\tau_i)$$

corresponds to simulated octafluoronapthalene peaks that occurring at times $\tau_i$ (i=1 ... n), $$g\sum_{j=1}^{m}\xi(t-t_j)$$

corresponds to simulated helium peaks $t_j$ (j=1 ... m), and $$g_0 \sum_{k=1}^{n_0(s)} \xi(t-t_k^{(0)}):$$

corresponds to real GCMS data peaks $t_k^{(0)}$ (k=1 ... $n_0$(s)).

Each of the above terms represents the response of a simulated or a real detector to octafluoronapthalene, helium, or combinations thereof. The terms $n_0(s)$, $\{t_k^{(0)}(s)\}_{k=1}^{n_0(s)}$ are the raw data ion arrival times. In some implementations, such arrival times can be pooled between successive scans (i.e., scan s and scan s+1). The terms m, n, $\{\tau_i\}$, $\{t_j\}$ are random variables that correspond to the octafluoronapthalene and helium simulations. The term "E" is an expectation value operator that averages over an ensemble of simulated data windows. In some implementations, each of the simulated data windows can include coupled scans and its own set of random variables.

Equation 4 can be rewritten as Equation 5.

$$\psi = g^2 \sum_{s=-3}^{3} F_2^{(s)}(\lambda_m, \mu, \gamma) + g_0^2 \sum_{s=-3}^{3} F_0^{(s)}(n_0(s), \{t_k^{(0)}(s)\}) + \qquad \text{Equation 5}$$
$$2gg_0 \sum_{s=-3}^{3} F_1^{(s)}(\lambda_m, \mu, \gamma; n_0(s), \{t_k^{(0)}(s)\})$$

Where the term $g_0$ is the median number of counts per single ion or neutral peak. The term $g_0$ can be fitted from the 0 fg data by examining the statistics of a large number of single ion/neutral peaks. In Equation 5, the first term represents simulated contributions to the response of the detector from octafluoronapthalene and helium, the middle term represents contributions from real GCMS data peaks, and the final term represents simulated contributions from octafluoronapthalene and helium as well as contributions from real GCMS data peaks.

Equation 4 involves an expectation value (E) and therefore must be used in conjunction with an appropriate joint Probability Distribution Function (PDF) of the relevant random variables (arrival times and numbers of arrivals). The arrival times for neutral helium can be represented using Poisson statistics. The arrival times for mass-selected octafluoronapthalene species can be represented using a combination of a normal distribution and a Poisson distribution. In some implementations, analytical approximations for incomplete Gaussian integrals can be used in the computations.

Equation 6 defines a new function f(x-y) in terms of the function zeta. Function f(x-y) can be used to make the subsequent algebra more compact.

$$\int_{-\infty}^{\infty} \xi(t-x)\xi(t-y)dt =: f(x-y) \qquad \text{Equation 6}$$

where ξ(t) represents the ion/neutral peaks on the m/z axis which are assumed to be detector pulses with unit peak height at t=0 and two slopes $b_1$ and $b_2$ as given by Equation 7. The terms $b_1$ and $b_2$ are determined by the detector's analog electronics.

$$\xi(t) = \begin{cases} e^{b_1 t} \to \text{if } (t \leq 0) \\ e^{b_2 t} \to \text{if } (t \geq 0) \end{cases} \quad \text{Equation 7}$$

The function f(x-y) is thus given by:

$$f(x-y) = \frac{1}{2b_1} e^{-b_1 |x-y|} + \frac{1}{2b_2} e^{-b_2 |x-y|} + \begin{cases} e^{-b_1 |x-y|} \cdot |x-y| \text{ if } b_1 = b_2 \\ \frac{1}{b_2 - b_1} [e^{-b_1 |x-y|} - e^{-b_2 |x-y|}] \text{ else} \end{cases} \quad \text{Equation 8}$$

Given that $\lambda(s) = \lambda_m \exp(-s^2/2)$, the term $F_0^{(s)}$ can be expressed as:

$$F_0^{(s)} \approx n_0(s) f(0) + 2 \left[ \sum_{1 \leq k_1 < k_2 \leq n_0(s)} f(t_{k_1}^{(0)} - t_{k_2}^{(0)}) \right] \quad \text{Equation 9}$$

the term $F_1^{(s)}$ can be expressed as:

$$F_1^{(s)} \approx E\left[-\sum_{i=1}^{n} \sum_{k=1}^{n_0(s)} f(\tau_i - t_k^{(0)}(s))\right] - E\left[-\sum_{j=1}^{m} \sum_{k=1}^{n_0(s)} f(t_j - t_k^{(0)}(s))\right]$$
$$\approx -\frac{\lambda(s)}{\gamma \sqrt{2\pi}} \sum_{k=1}^{n_0(s)} \int_{-\infty}^{\infty} d\tau e^{-\tau^2/(2\gamma^2)} f(\tau - t_k^{(0)}(s)) - \mu n_0(s) \int_{-\infty}^{\infty} f(t) dt \quad \text{Equation 10}$$

the term $F_2^{(s)}$ can be expressed as:

$$F_2^{(s)} \approx E\left[(m+n) f(0) + 2\left[\sum_{1 \leq i_1 < i_2 \leq n} f(\tau_{i_1} + \tau_{i_2})\right] + 2\left[\sum_{1 \leq j_1 < j_2 \leq m} f(t_{j_1} + t_{j_2})\right] + 2\sum_{i=1}^{n} \sum_{j=1}^{m} f(t_j - \tau_i)\right]$$
$$\approx f(0)[\lambda(s) + 5\mu] + \frac{(\lambda(s))^2}{2\gamma \sqrt{\pi}} \int_{-\infty}^{\infty} e^{-x^2/(4\gamma^2)} f(x) dx + 5\mu^2 \int_{-\infty}^{\infty} f(x) dx + 2\mu \lambda(s) \int_{-\infty}^{\infty} f(x) dx \quad \text{Equation 11}$$

and the expectation value operator "E" can be expressed as:

$$E(f(\tau_{i_1} - \tau_{i_2})) \approx \frac{1}{2\gamma \sqrt{\pi}} \int_{-\infty}^{\infty} e^{-x^2/(4\gamma^2)} f(x) dx \quad \text{Equation 12}$$

or $$E(f(t_{j_1} + t_{j_2})) \approx \frac{1}{5} \int_{-\infty}^{\infty} f(x) dx \quad \text{Equation 13}$$

or $$E(f(t_j + \tau_i)) \approx \frac{1}{5} \int_{-\infty}^{\infty} f(x) dx \quad \text{Equation 14}$$

Thus, for any s, the term $F_2^{(s)}$ can be expressed as a positive definite quadratic in $\lambda_s$ and $\mu$.

Once the window objective function has been optimized (using, e.g., a Nelder-Mead procedure, as discussed further below), it can be derived by substituting Equation 9 into Equation 6 and denoting the following:

$$f_0 := f(0) \quad \text{Equation 15}$$

$$f_1 := \int_{-\infty}^{\infty} f(t) dt \quad \text{Equation 16}$$

$$f_2(\gamma) := \frac{1}{2\gamma \sqrt{\pi}} \int_{-\infty}^{\infty} e^{-x^2/(4\gamma^2)} f(x) dx \quad \text{Equation 17}$$

$$H(t; \gamma) := \int_{-\infty}^{\infty} e^{-x^2/(2\gamma^2)} f(x-t) \frac{dx}{\gamma \sqrt{2\pi}} \quad \text{Equation 18}$$

In particular, the window object function becomes:

$$\Psi^*(\lambda_m, \mu, \gamma) = \quad \text{Equation 19}$$
$$\text{termindep.of}(\lambda_m, \mu, \gamma) - \left\{ \lambda_m \sum_{s=-3}^{3} e^{-s^2/2} \sum_{k=1}^{n_0(s)} H(t_k^{(0)}(s); \gamma) + (g_0)^2 \frac{\left\{\mu f_1 \sum_{s=-3}^{3} n_0(s)\right\}^2}{f_0 \left(\lambda_m \sum_{s=-3}^{3} e^{-s^2} + 35\mu\right) + f_2(\gamma) \sum_{s=-3}^{3} e^{-s^2} \gamma_m^2 + 35\mu^2 f_1 + 2\lambda_m \mu f_1 \sum_{s=-3}^{3} e^{-s^2/2}} \right\}$$

Solving for $\lambda_m^*(\gamma)$ and $\mu(\gamma)$ yields:

$$A := \sum_{s=-3}^{3} e^{-s^2/2} \sum_{k=1}^{n_0(s)} H(t_k^{(0)}(s); \gamma) \quad \text{Equation 20}$$

$$B := f_1 \sum_{s=-3}^{3} n_0(s) \quad \text{Equation 21}$$

$$C_{11} := f_0 \sum_{s=-3}^{3} e^{-s^2/2}, \quad \text{Equation 22}$$

$$C_{12} := 35 f_0 \quad \text{Equation 23}$$

$$D_1 := f_2(\gamma) \sum_{s=-3}^{3} e^{-s^2}, \quad \text{Equation 24}$$

-continued $$D_2 := 35 f_1,$$  Equation 25

$$D_3 := f_1 \sum_{s=-3}^{3} e^{-s^2/2}$$  Equation 26 so that $$\Psi^* = const - (g_0)^2 \frac{\{A\lambda_m + B\mu\}^2}{[C_1\lambda_m + C_2\mu + D_1\lambda_m^2 + D_2\mu^2 + 2D_3\lambda_m\mu]}$$  Equation 27 where $\lambda_m \geq 0$, and $\mu \geq 0$ Please note that a g* may be $\geq 0$ if the three parameters $\lambda_m$, $\mu$, and $\gamma$, are not optimized together by setting $g=g_0$.

Using Equation 5 and setting $g=g_0$, the function to be minimized becomes:

$$\frac{1}{(g_0)^2} \Psi(\lambda_m, \mu, \gamma) = \sum_{s=-3}^{3} F_2^{(s)} + 2 \sum_{s=-3}^{3} F_1^{(s)} + const$$  Equation 28 since the $F_0$ term does not depend on the parameters to be optimized (i.e., $\lambda_m$, $\mu$, and $\gamma$).

By combining Equation 9 and Equations 20-26, $$-\sum_s F_1^{(s)} = A\lambda_m + B\mu,$$  Equation 29

$$\sum_s F_2^{(s)} = C_1\lambda_m + C_2\mu + D_1\lambda_m^2 + D_2\mu^2 + 2D_3\lambda_m\mu$$  Equation 30

Thus, the window objective function $\Psi$ is a positive-definite quadratic and possesses a single global minimum in the $\lambda_m$, $\mu$ planes for fixed $\gamma$. The location of the optimum, which can be denoted as $\lambda_m^*(\gamma)$, $\mu^*(\gamma)$, depends on mass-selected and non-mass-selected arrival-time arrays and can be determined by setting $d\Psi/d\lambda_m = d\Psi/d\mu = 0$, which results in a non-singular system of linear equations:

$$\begin{bmatrix} D_1 & D_3 \\ D_3 & D_2 \end{bmatrix} \begin{bmatrix} \lambda_m^* \\ \mu^* \end{bmatrix} = \begin{bmatrix} A - \frac{C_1}{2} \\ B - \frac{C_2}{2} \end{bmatrix}$$  Equation 31

The solution to Equation 31 is given by:

$$\lambda_m^*(\gamma) = \frac{D_2(2A - C_1) - D_3(2B - C_2)}{2(D_1 D_2 - D_3^2)}$$  Equation 32

$$\mu^*(\gamma) = \frac{D_1(2B - C_2) - D_3(2A - C_1)}{2(D_1 D_2 - D_3^2)}$$  Equation 33 in which A and B are determined by the algorithm from the experimentally observed numbers and arrival times of the ions and neutrals.

When this is substituted into Equations 29, 30, the window objective function $\Psi$ is given by:

$$\psi(\lambda_m^*(\gamma), \mu^*(\gamma), \gamma) = -\frac{1}{4(D_1 D_2 - D_3^2)} \left\{ \begin{array}{l} D_1(2B - C_2)^2 + \\ D_2(2A - C_1)^2 - \\ 2D_3(2A - C_1)(2B - C_2) \end{array} \right\}$$  Equation 34

Please note that, in Equation 34, only A and $D_1$ are a function of $\gamma$. The window objective function $\Psi$ is minimized with respect to $\gamma$ for given $n_0(s)$, $t_c^{(o)}(s)$ data to find initialization values for: $\lambda_m^* = \lambda_m^*(\gamma)$, $\mu^* = \mu^*(\gamma)$ and $\gamma^*$. This final optimization can accommodate jitter can, in some implementations, can be performed numerically.

In some implementations, the analysis of information gathered using multiple analytical techniques can be optimized by optimizing "tuning parameters" that characterize the analytical techniques. In some implementations, the tuning parameters can be optimized once per class of analytical technique, such as for GCMS analysis in a standard scan (as opposed to fast scan) mode. Examples of such parameters include:

the electronic noise floor of the detector, which can be expressed in counts. For example, the electronic noise floor of a detector can be around 6.6 counts.

the term "b" in equation 2, which can be expressed as a number of scans. For example, the term "b" can be approximately 0.

the term "c" in equation 2, which can be expressed as a number of scans squared For example, the term "c" can be approximately 1 scan$^2$.

the terms "$b_1$", "$b_2$" in equation 7, which can be expressed in units of amu$^{-1}$. For example, the terms "$b_1$" can be approximately equal to "$b_2$" and approximately equal to 4 (0.1 amu)$^{-1}$.

the term "f(s)" which can be given as $\exp(-s^2/2)$.

a first window dimension, which can be denoted as a term "$n_1$" and expressed in units of amu.

a second window dimension, which can be denoted as a term "$n_2$" and expressed in units of scan number.

a first coordinate of the focus of the window objective function, which can be denoted as a term "$m_1$" and expressed in units of amu.

a second coordinate of the focus of the window objective function, which can be denoted as a term "$m_2$" and expressed in units of scan number.

In some implementations (such as cascaded implementations), some tuning parameters can be vectorized per each iteration. For example, the parameters $b_1$, $b_2$, b, c, $n_1$, $n_2$, $m_1$, and $m_2$ can be vectorized.

For the optimum value of window objective function $\Psi$ at the maximum, $d\Psi = 0$. Therefore:

$$g^*(\lambda_m, \mu, \gamma) = -g_0 \sum_{s=-3}^{3} F_1^{(s)} / \sum_{s=-3}^{3} F_2^{(s)}$$  Equation 35

$$\psi(\lambda_m, \mu, \gamma, g^*) = \psi(\lambda_m, \mu, \gamma)$$  Equation 36

$$= g_0^2 \left[ \sum_{s=-3}^{3} F_0^{(s)} - (\sum_{s=-3}^{3} F_1^{(s)})^2 / \sum_{s=-3}^{3} F_2^{(s)} \right]$$

$F_0$, $F_1$, $F_2$ can be evaluated analytically at low concentrations and used in Equation 6. The window objective function $\Psi^*$ can be minimized over $\lambda_m$, $\mu$, $\gamma$ to find $\lambda_m^*(\lambda)$, $\mu^*(\gamma)$, $\gamma^*$, which can be plugged into g*.

Figure 5:
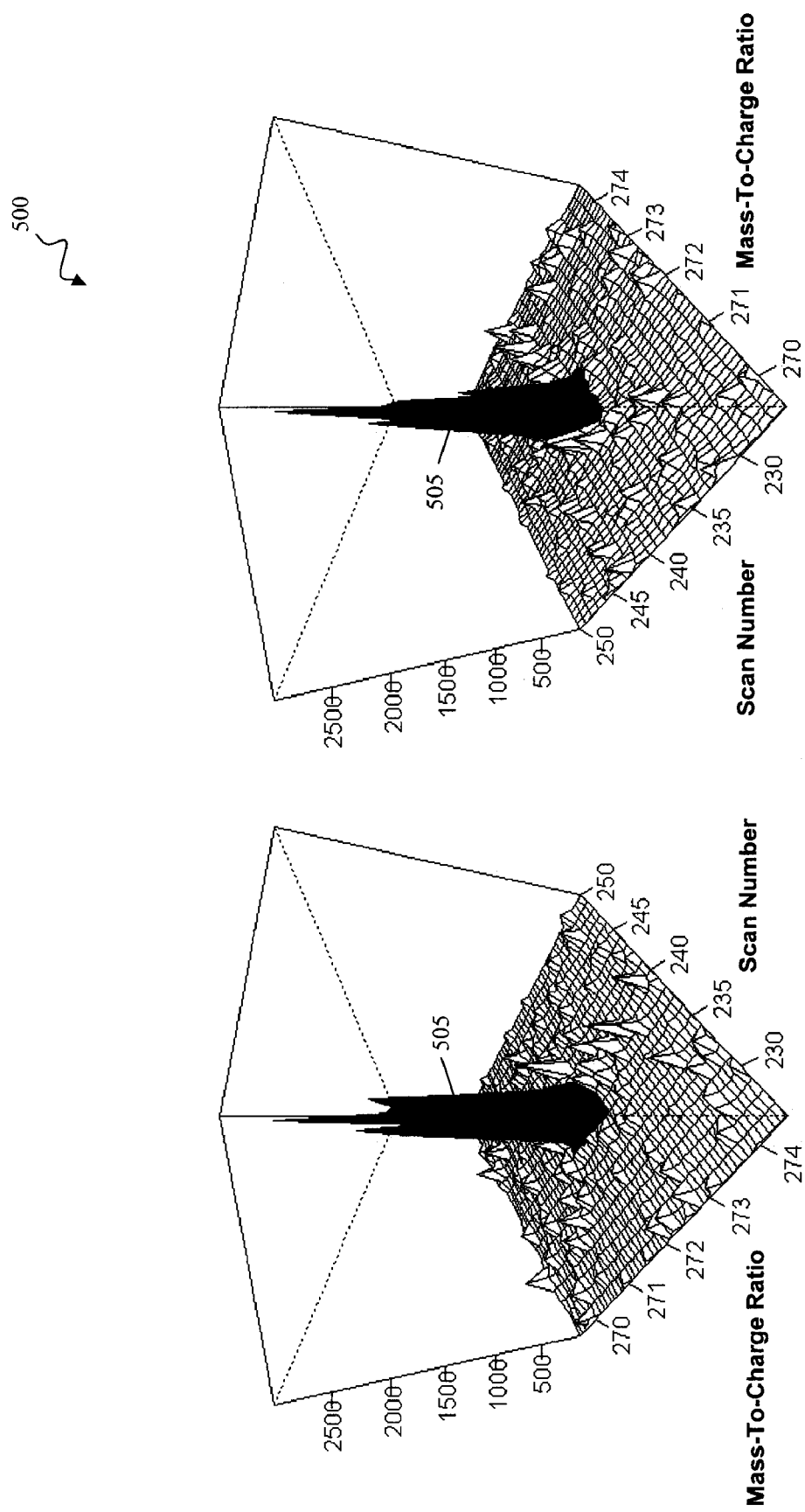
FIG. 5 is a graph that represents raw GCMS data collected on a sample that includes 1000 fg octafluoronapthalene in a helium carrier.

Illustrative examples of the results that can be obtained using the described systems and techniques to analyze information gathered using multiple analytical techniques are now described. FIG. 5 is a graph 500 (shown from two different vantage points) that represents raw GCMS data collected on a sample that includes 1000 fg octafluoronapthalene in a helium carrier. At this concentration, an octafluoronapthalene peak 505 is easy to resolve on the analytical information surface.

Figure 6:
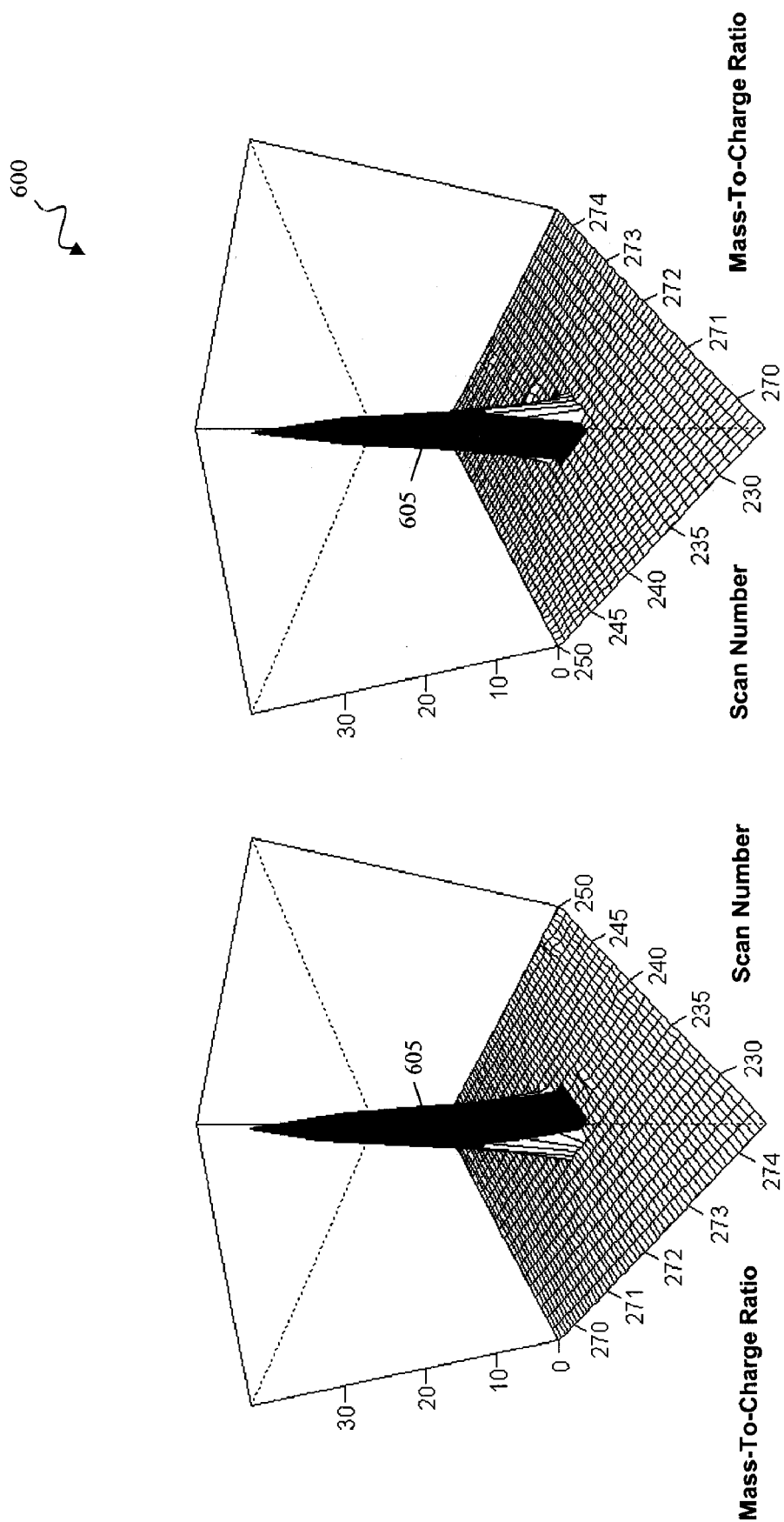
FIG. 6 is a graph that represents the $\lambda$ derivate surface that was estimated using the raw GCMS data represented in the graph of FIG. 5.

FIG. 6 is a graph 600 that represents the $\lambda$ derivate surface estimated using the approach discussed above and the raw GCMS data represented in graph 500 (FIG. 5). As can be seen, a peak 605 that corresponds to an estimate of the quantity of mass-selected octafluoronapthalene species is easy to resolve on the $\lambda$ derivative surface.

In some implementations, raw GCMS data such as shown in graph 500 can be used to calibrated global tuning parameters. Once calibration is complete, these parameters can be used in analyzing raw GCMS data in which peaks such as peak 505 are not as ease to resolve.

Figure 7:
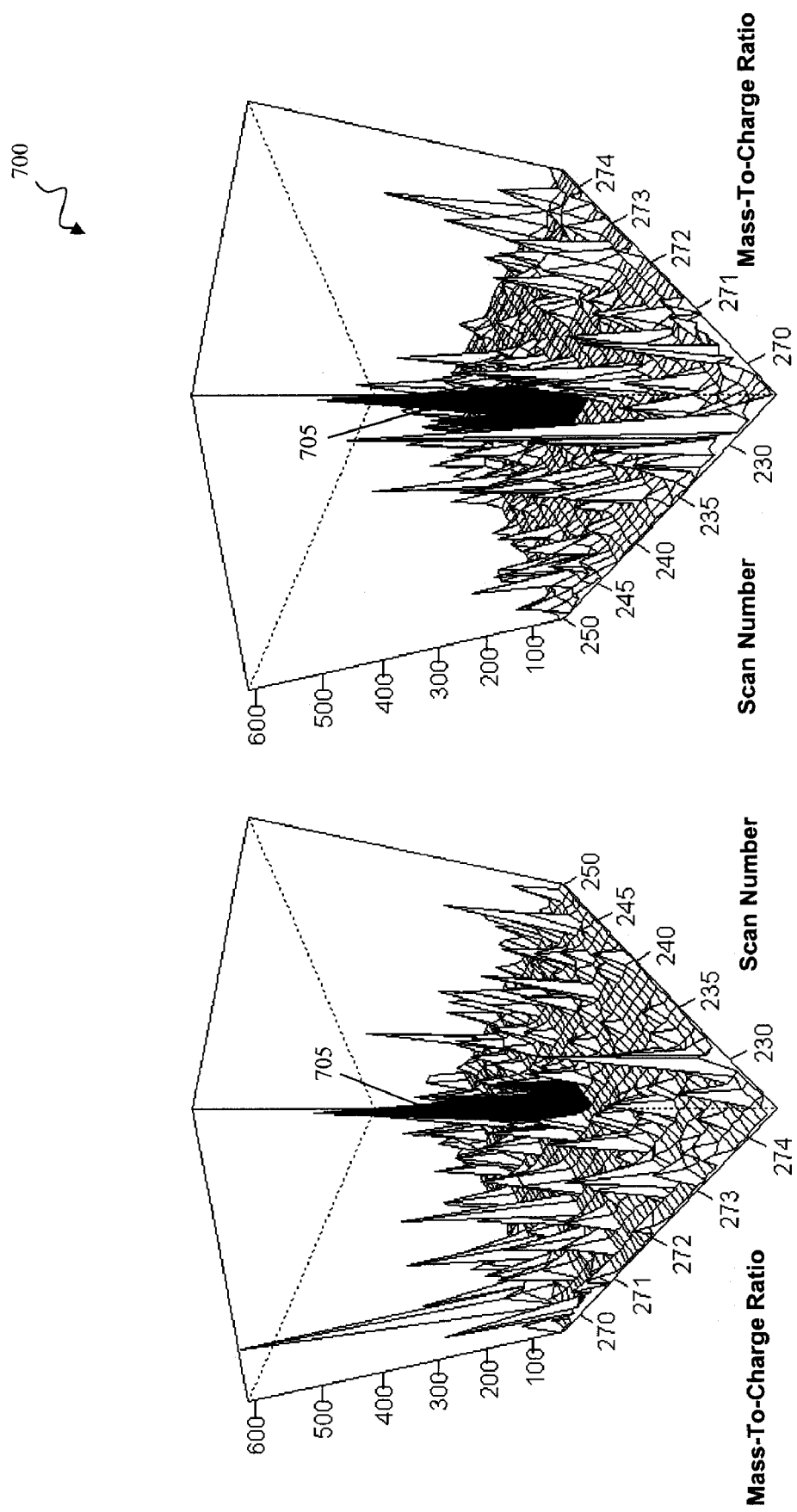
FIG. 7 is a graph that represents raw GCMS data collected on a sample that includes 100 fg octafluoronapthalene in a helium carrier.

FIG. 7 is a graph 700 that represents raw GCMS data collected on a sample that includes 100 fg octafluoronapthalene in a helium carrier. At this concentration, an octafluoronapthalene peak 505 is more difficult to resolve on the analytical information surface.

Figure 8:
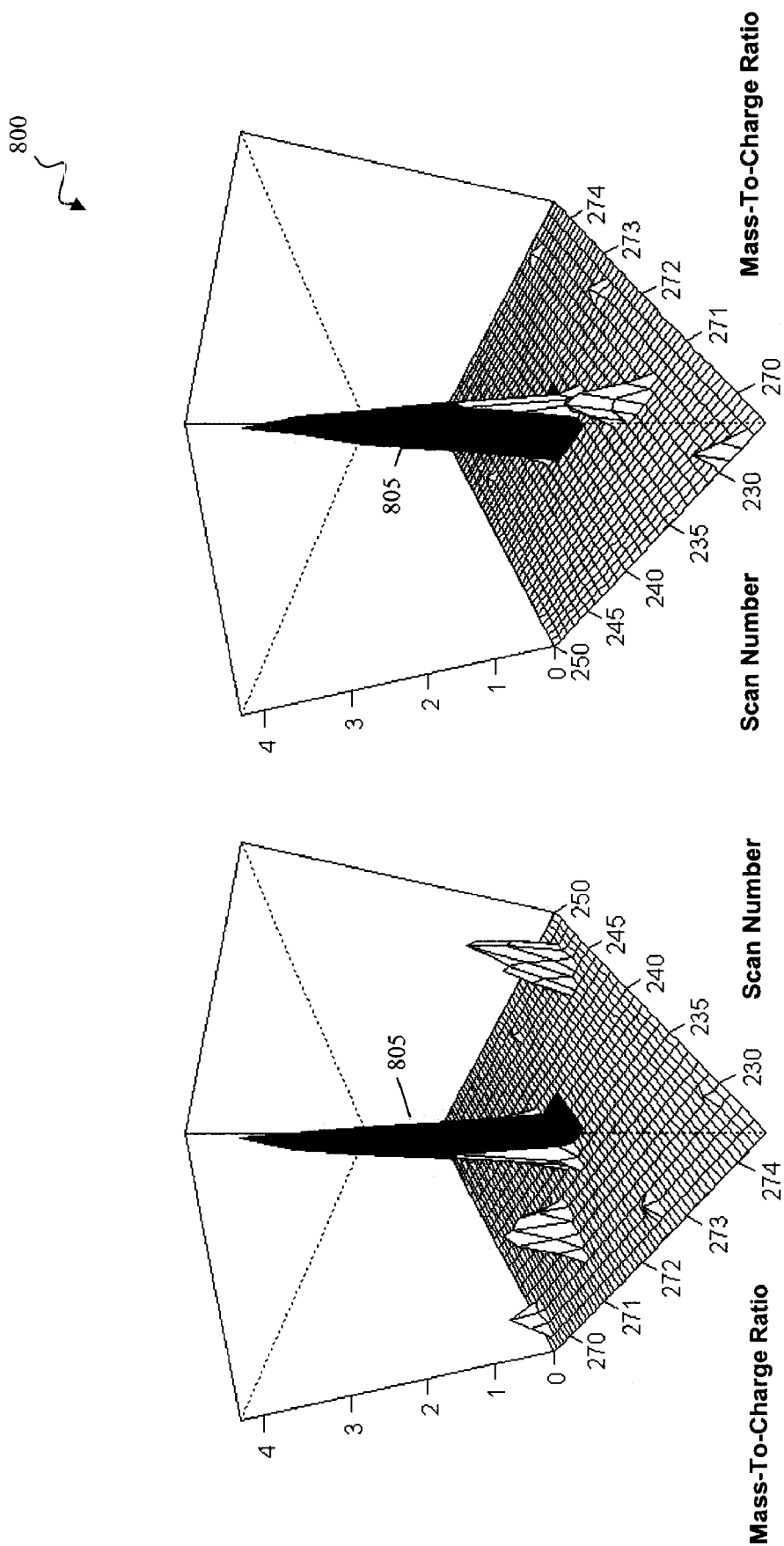
FIG. 8 is a graph that represents the $\lambda$ derivate surface that was estimated using the raw GCMS data represented in the graph of FIG. 7.

FIG. 8 is a graph 800 that represents the $\lambda$ derivate surface estimated using the approach discussed above and the raw GCMS data represented in graph 700 (FIG. 7). As can be seen, a peak 805 that corresponds to an estimate of the quantity of mass-selected octafluoronapthalene species is easy to resolve on the $\lambda$ derivative surface.

Figure 9:
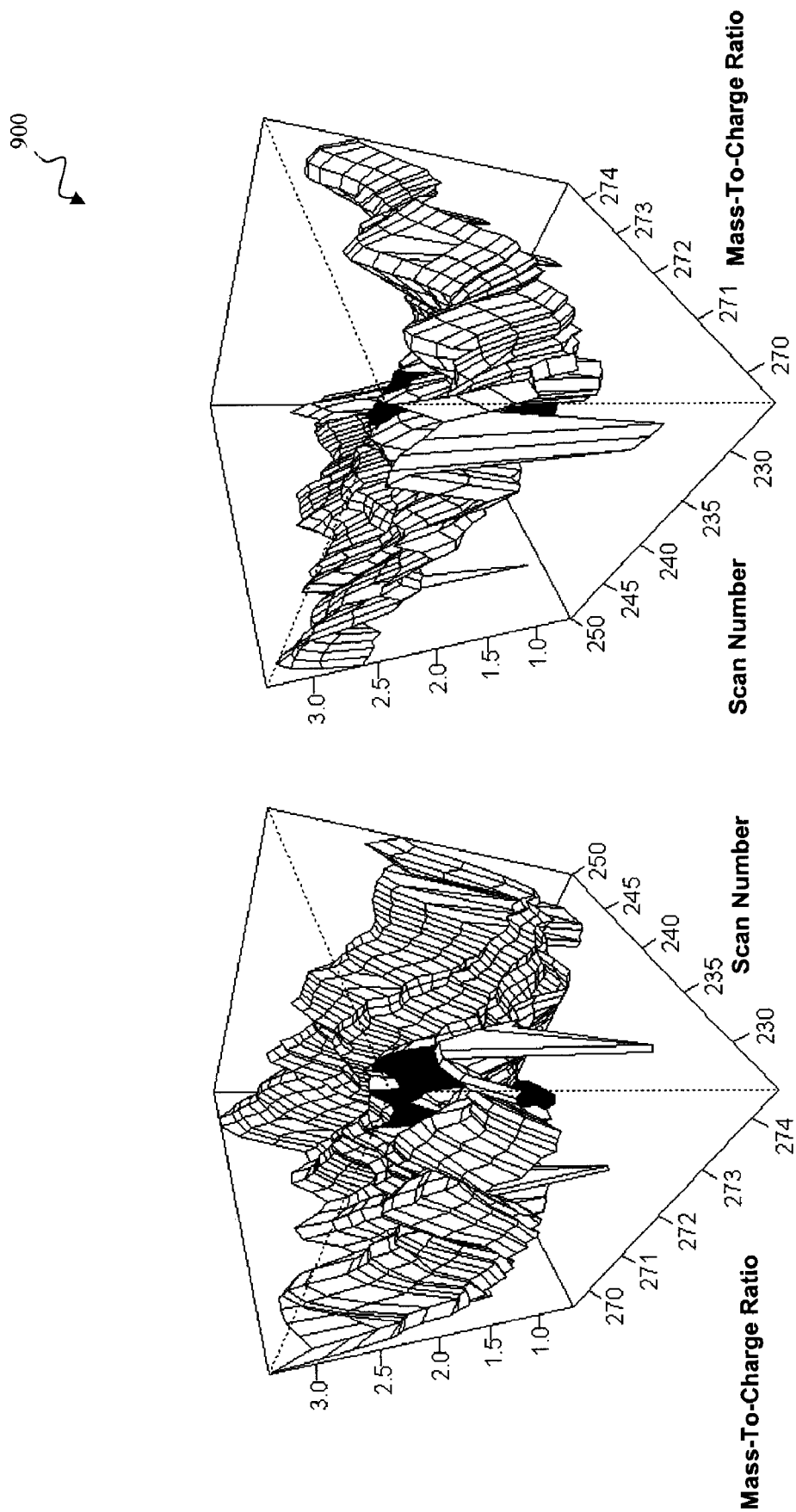
FIG. 9 is a graph that represents the $\mu$ derivate surface that was estimated using the raw GCMS data represented in the graph of FIG. 7.

FIG. 9 is a graph 900 that represents the $\mu$ derivate surface estimated using the approach discussed above and the raw GCMS data represented in graph 700 (FIG. 7). As can be seen, peaks corresponding to an estimate of the quantity of non-mass-selected helium are distributed across the $\mu$ derivative surface, as would be expected without mass selection.

Figure 10:
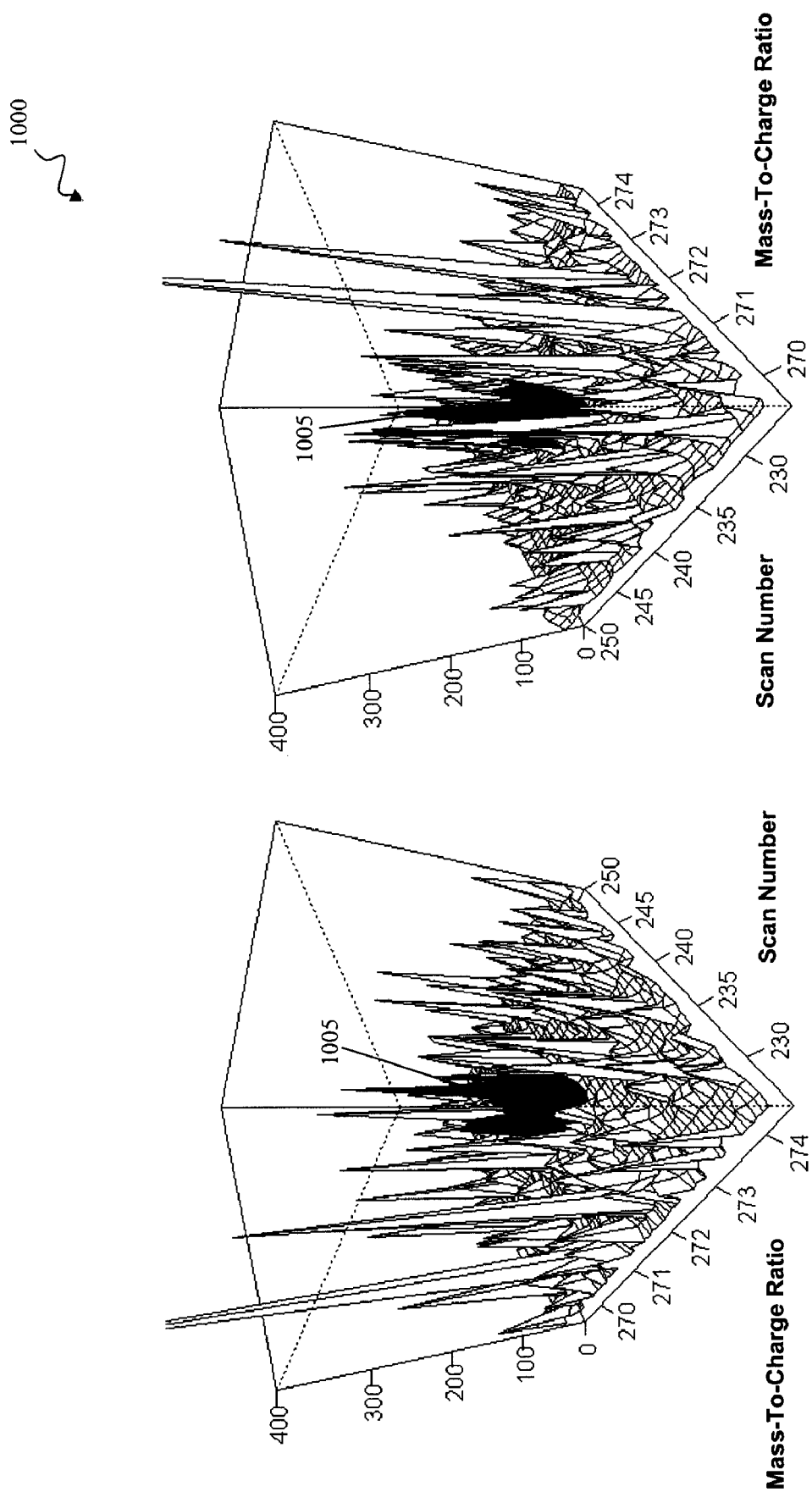
FIG. 10 is a graph that represents raw GCMS data collected on a sample that includes 20 fg octafluoronapthalene in a helium carrier.

FIG. 10 is a graph 1000 that represents raw GCMS data collected on a sample that includes 20 fg octafluoronapthalene in a helium carrier. At this concentration, an octafluoronapthalene peak 1005 is very difficult to resolve on the analytical information surface.

Figure 11:
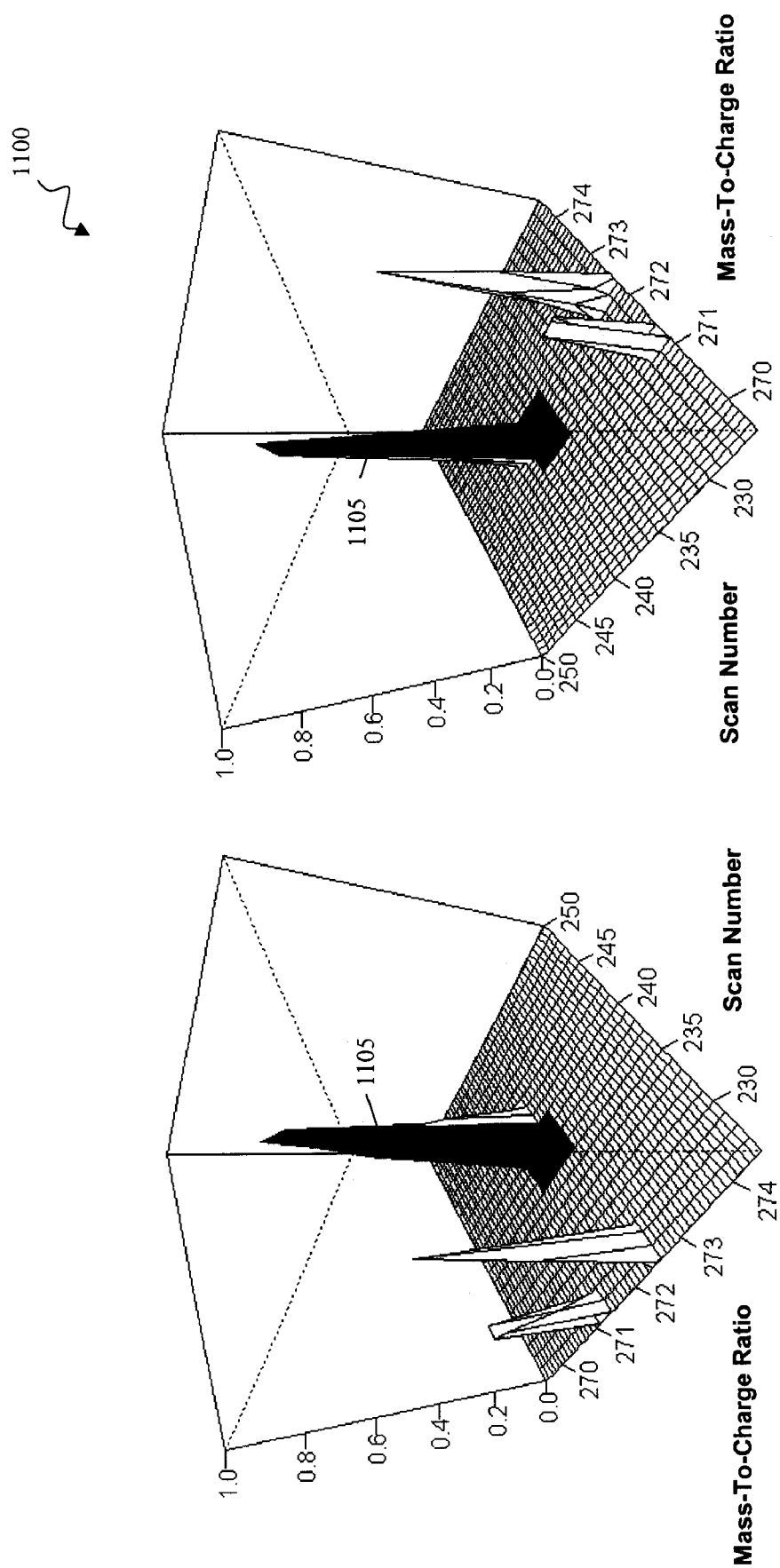
FIG. 11 is a graph that represents the $\lambda$ derivate surface that was estimated using the raw GCMS data represented in the graph of FIG. 10.

FIG. 11 is a graph 1100 that represents the $\lambda$ derivate surface estimated using the approach discussed above and the raw GCMS data represented in graph 1000 (FIG. 10). As can be seen, a peak 1105 that corresponds to an estimate of the quantity of mass-selected octafluoronapthalene species is easy to resolve on the $\lambda$ derivative surface.

Figure 12:
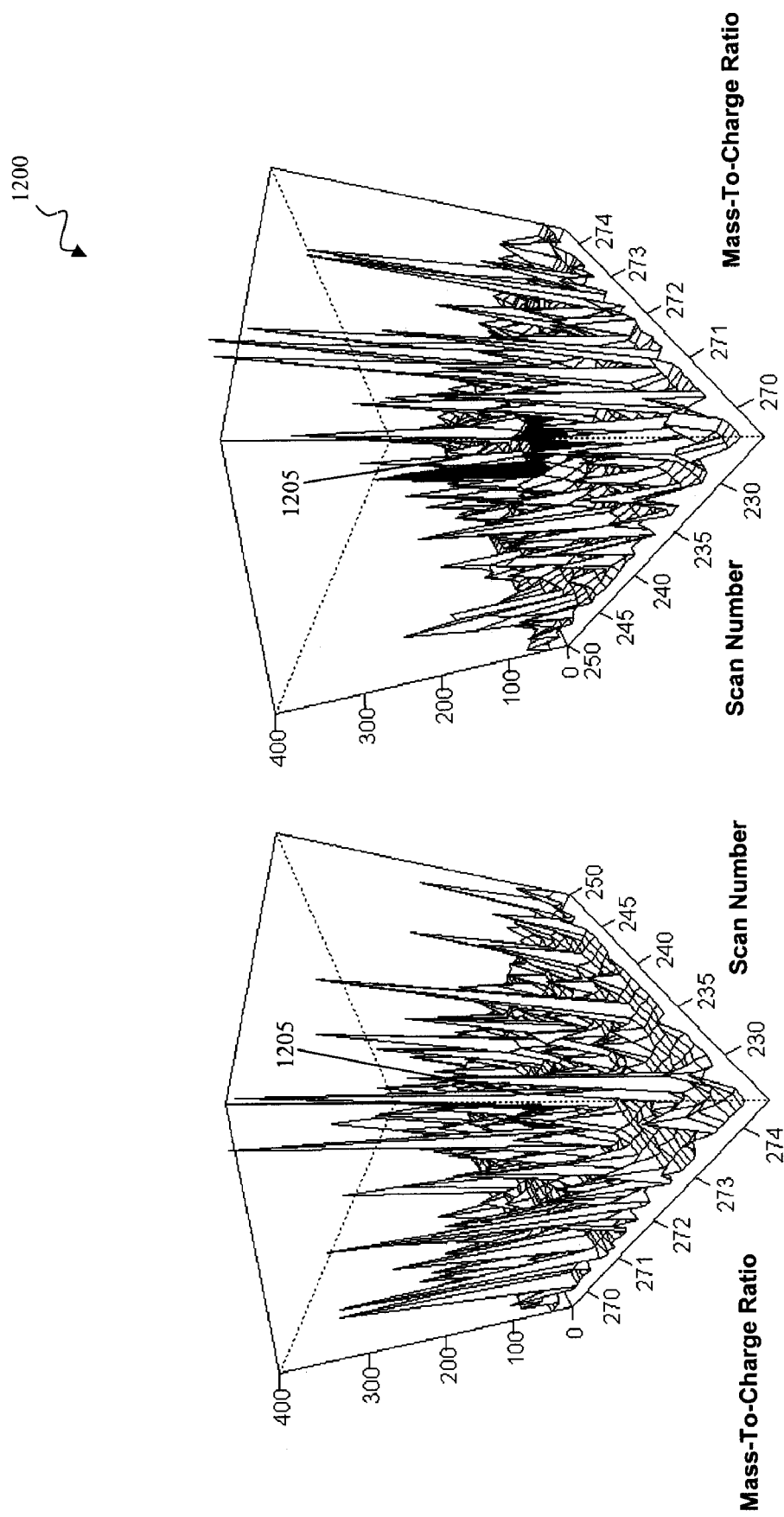
FIG. 12 is a graph that represents raw GCMS data collected on a helium carrier sample that does not include octafluoronapthalene.

FIG. 12 is a graph 1200 that represents raw GCMS data collected on a helium carrier sample that does not include octafluoronapthalene. At zero concentration, no octafluoronapthalene peak should be present and the position 1205 where octafluoronapthalene peaks are found in graphs 500 (FIG. 5), 700 (FIG. 7) and 1000 (FIG. 10) should be indistinguishable from the remainder of the analytical information surface.

Figure 13:
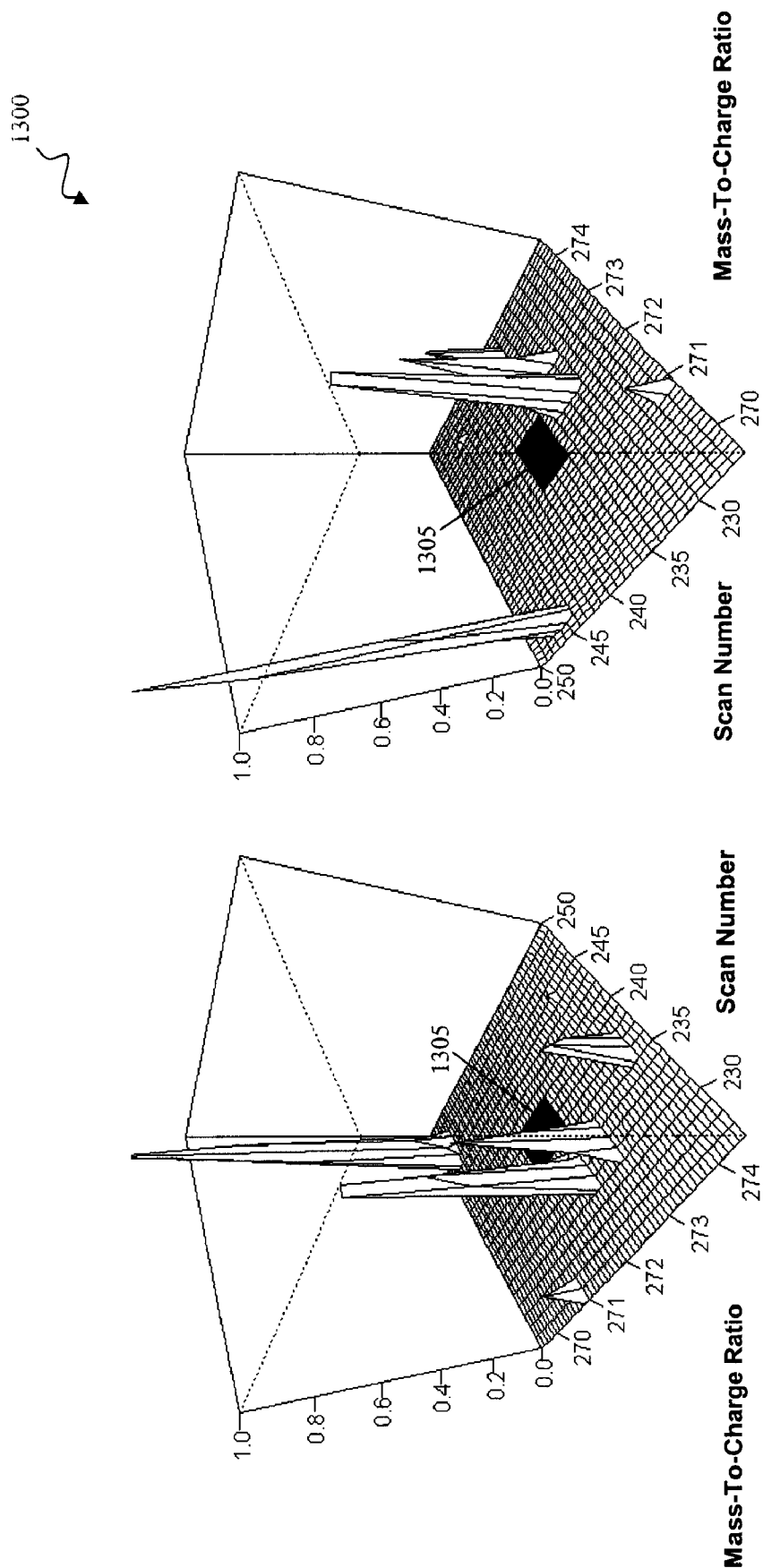
FIG. 13 is a graph that represents the $\lambda$ derivate surface that was estimated using the raw GCMS data represented in the graph of FIG. 12.

FIG. 13 is a graph 1300 that represents the $\lambda$ derivate surface estimated using the approach discussed above and the raw GCMS data represented in graph 1200 (FIG. 12). As can be seen, the position 1205 where estimates of the quantity of mass-selected octafluoronapthalene species are found in graphs 600 (FIG. 6), 800 (FIG. 8) and 1100 (FIG. 11) is largely indistinguishable from the remainder of the $\lambda$ derivative surface.

Figure 14:
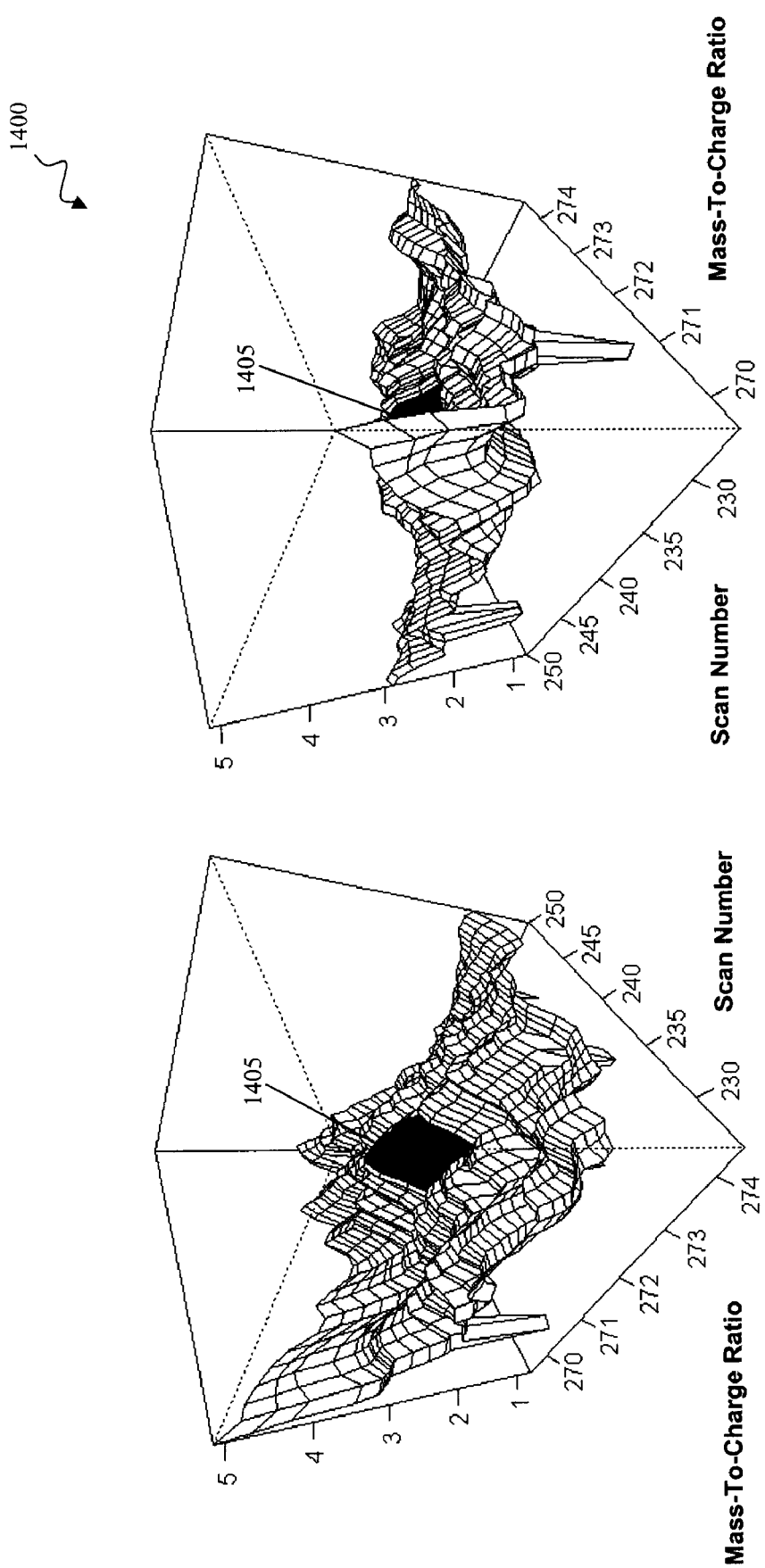
FIG. 14 is a graph that represents the $\mu$ derivate surface that was estimated using the raw GCMS data represented in the graph of FIG. 12.

FIG. 14 is a graph 1400 that represents the $\mu$ derivate surface estimated using the approach discussed above and the raw GCMS data represented in graph 1200 (FIG. 12). As can be seen, peaks corresponding to an estimate of the quantity of non-mass-selected helium are distributed across the $\mu$ derivative surface, as would be expected without mass selection.

Various implementations of the systems and techniques described here can be realized in digital electronic circuitry, integrated circuitry, specially designed ASICs (application specific integrated circuits), computer hardware, firmware, software, and/or combinations thereof. These various implementations can include one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) may include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

A number of implementations have been described. Nevertheless, it will be understood that various modifications may be made. Accordingly, other implementations are within the scope of the following claims.

What is claimed is:

1. An article comprising one or more computer-readable media storing instructions operable to cause one or more machines to perform operations for analyzing information gathered by multiple analytical techniques, the operations comprising:

sweeping a window objective function across a multidimensional analytical information space that represents information gathered by multiple analytical techniques;

inferring a derivative attribute for each of a collection of positions along the sweep using the window objective function and the information gathered by the multiple analytical techniques;

combining the derivative attributes for the collection of positions into a derivative space; and making the derivative space available for analyzing information gathered by multiple analytical techniques.

2. The article of claim 1, wherein the operations further comprise assigning the derivative attributes to foci of the window objective function at each of the positions in the collection of positions.

3. The article of claim 1, wherein:
the analytical information space comprises a two-dimensional surface;
the window objective function comprises a two-dimensional window objective function; and
combining the derivative attributes comprises combining the derivative attributes into a derivative surface.

4. The article of claim 1, wherein the analytical information space represents a mass-to-charge ratio of charged species generated from a sample and interactions between constituent components of the sample and a stationary phase.

5. The article of claim 1, wherein sweeping the window objective function comprises sweeping a function that includes a parameter representing simulated mass-selected information and a parameter representing non-mass-selected information.

6. The article of claim 1, wherein combining the derivative attributes comprises combining derivative attributes representing mass-selected species into the derivative space.

7. The article of claim 1, wherein inferring the derivative attribute comprises generating a maximum a posteriori (MAP) estimation of the value of the derivative attribute.

8. The article of claim 1, wherein making the derivative space available comprises providing the derivative space to an allied data processing device.

9. The article of claim 1, wherein making the derivative space available comprises outputting the derivative space for display to a human user.

10. The article of claim 1, wherein the operations further comprise estimating a value of the sample parameter based on the derivative space.

11. The article of claim 10, wherein estimating the value of the sample parameter comprises estimating the value using Bayesian statistics.

12. The article of claim 10, wherein estimating the value of the sample parameter comprises generating a maximum a posteriori (MAP) estimation of the value of the sample parameter.

13. The article of claim 1, wherein sweeping the window objective function comprises sweeping a function that includes a parameter representing simulated mass-selected information.

14. The article of claim 1, wherein sweeping the window objective function comprises sweeping a function that includes a parameter representing non-mass-selected information.

15. The article of claim 1, wherein sweeping the window objective function comprises sweeping a function that includes a parameter representing real chromatographic information.

16. The article of claim 1, wherein sweeping the window objective function comprises determining a collection of derivative attributes at different positions.

17. An article comprising one or more computer-readable media storing instructions operable to cause one or more machines to perform operations for analyzing information gathered by multiple analytical techniques, the operations comprising:
sweeping a window objective function across an analytical information space that represents information gathered by multiple analytical techniques;
inferring a derivative attribute for each of a collection of positions along the sweep using the window objective function and the information gathered by the multiple analytical techniques, wherein inferring the derivative attribute comprises generating a maximum a posteriori (MAP) estimation of the value of the derivative attribute; and
combining the derivative attributes for the collection of positions into a derivative space; and
making the derivative space available for analyzing information gathered by multiple analytical techniques.

* * * * *

UNITED STATES PATENT AND TRADEMARK OFFICE
CERTIFICATE OF CORRECTION

PATENT NO. : 7,571,056 B2  Page 1 of 1
APPLICATION NO. : 11/753444
DATED : August 4, 2009
INVENTOR(S) : Shahar Ben-Menahem et al.

It is certified that error appears in the above-identified patent and that said Letters Patent is hereby corrected as shown below:

Title Page, Col. 1 Item [75] (Inventors), Line 1 – Delete "Pasadena, CA" and insert -- Mountain View, CA --, therefore.

Title Page, Col. 2 Item [56] (Other Publications), Line 11 – Delete "form" and insert -- from --, therefore.

Title Page, Col. 2 Item [56] (Other Publications), Line 15 – Delete "form" and insert -- from --, therefore.

Title Page, Col. 2 Item [56] (Other Publications), Line 18 – Delete "form" and insert -- from --, therefore.

Signed and Sealed this

Twenty-ninth Day of September, 2009

David J. Kappos
*Director of the United States Patent and Trademark Office*